United States Patent [19]

Borschneck

[11] Patent Number: 4,941,465
[45] Date of Patent: Jul. 17, 1990

[54] ISCHIAL PERINEAL CUSHION FOR EMERGENCY TRACTION SPLINT

[76] Inventor: Anthony G. Borschneck, 770 Flower Ash La., Redding, Calif. 96003

[21] Appl. No.: 313,214

[22] Filed: Feb. 21, 1989

[51] Int. Cl.⁵ .................... A61F 5/04; A61F 5/28; A61F 5/02
[52] U.S. Cl. .................... 128/87 R; 128/88; 128/99.1; 128/100.1; 128/78
[58] Field of Search .............. 128/87 R, 87 A, 87 C, 128/88, 89 R, 78, 99.1, 100.1, 101.1; 2/338

[56] References Cited

U.S. PATENT DOCUMENTS

| | | | |
|---|---|---|---|
| 1,050,258 | 1/1913 | Ullery | 128/85 |
| 1,389,525 | 8/1921 | Mosby | 128/85 |
| 1,479,535 | 1/1924 | Ferragamo | 128/85 |
| 1,573,296 | 2/1926 | Brasell | 128/85 |
| 1,577,712 | 3/1926 | Graham | 128/85 |
| 2,198,908 | 4/1940 | Ellis | 128/85 |
| 3,756,227 | 9/1973 | Sager | 128/84 C |
| 3,906,942 | 9/1975 | Lumb | 128/84 C |
| 4,265,230 | 5/1981 | Jordon | 128/84 C |
| 4,608,971 | 9/1986 | Borschneck | 128/84 C |

Primary Examiner—Robert A. Hafer
Assistant Examiner—K. Owens
Attorney, Agent, or Firm—Lothrop & West

[57] ABSTRACT

In order to distribute the countertraction forces exerted on the perineal region by a cushion mounted on a lower limb emergency traction splint, the cushion is formed to an elongated saddle shape with enlarged lobes on opposite ends. The cushion is made laterally bendable so that when applied to the patient, the cushion impinges against the ischial tuberosity, the ischial and pubic rami and the midline symphysis pubic. Patient comfort and splint security are thereby enhanced.

8 Claims, 2 Drawing Sheets

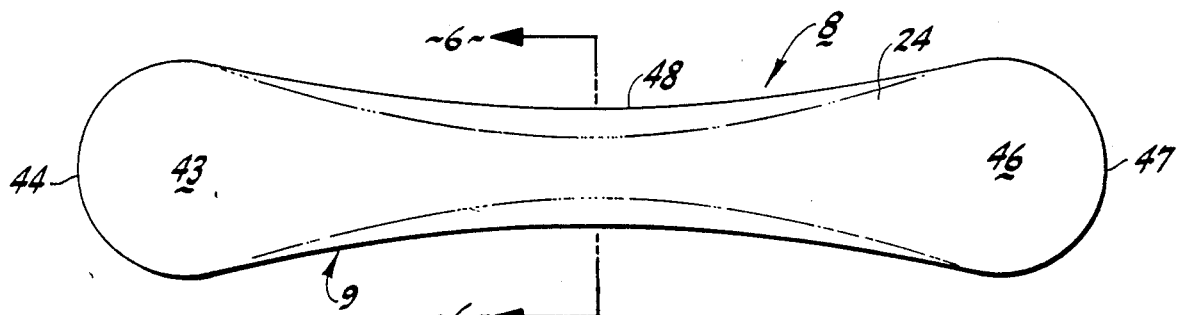
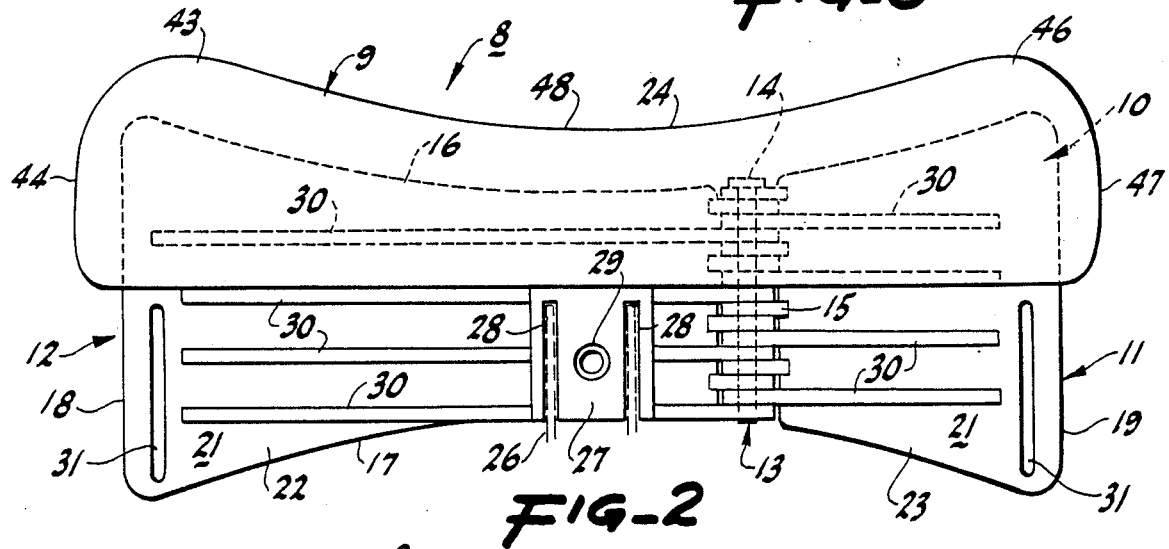
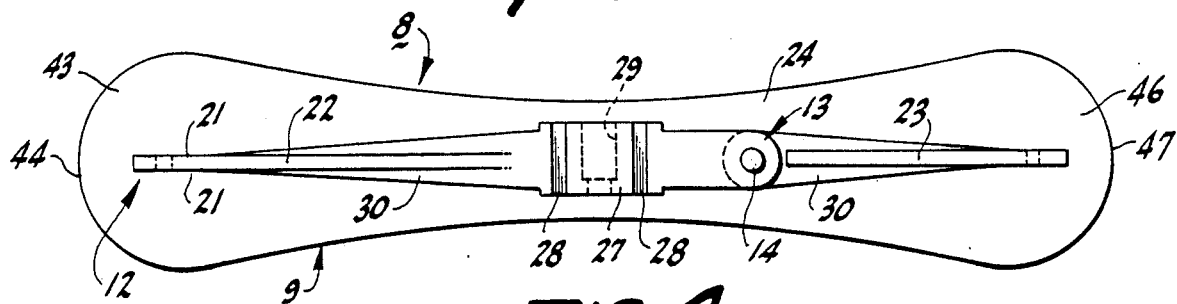
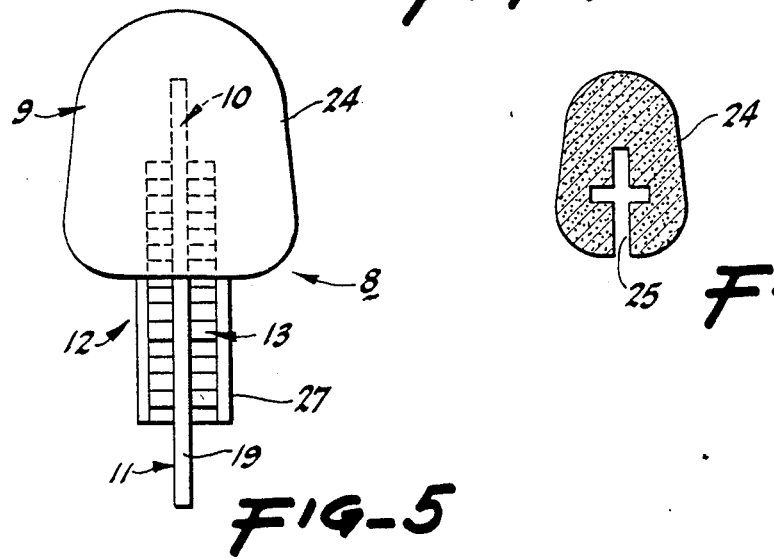
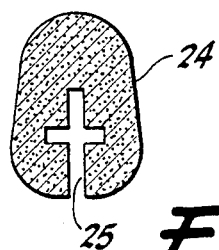

ISCHIAL PERINEAL CUSHION FOR EMERGENCY TRACTION SPLINT

BACKGROUND OF THE INVENTION

1. Field of the Invention

The invention relates to padded cushions, or crotch pieces, for lower limb emergency traction splints.

2. Prior Art

The human pelvis is strong and massively constructed. It is the foundation for the torso and support for lower limb attachment and locomotion. It is shaped so that its ischial tuberosity forms a platform for sitting in an upright position.

The tuberosity is medial to the shaft of the femur and is located half the distance between the midline symphysis pubis and the femoral shaft. In supine attitude, the shaft of the human femur lies on substantially the same horizontal plane as the ischial tuberosity. This anatomical characteristic has been utilized to advantage in various prior art emergency traction splints.

The classical Thomas Full Ring Splint has been available since 1875. It is the most correct splint anatomically and physiologically, providing countertraction not only on the ischial tuberosity but also on the ischial ramus, the pubic ramus and/or the mid line symphysis pubis. Countertraction is never lost because when the ring is angled 55 degrees to the shaft of the femur the ring forms a saddle for the perineum.

The Thomas Full Ring Splint, however, is not without disadvantages. The patient's leg must be lifted and, at considerable discomfort to the patient, threaded onto the ring in order to apply the splint. Many sizes of splint are needed to cover all sizes of patients. Application time is long; and, once splinted, the patient is immobilized in an outsized, cumbersome and awkward device. Further, the Thomas Full Ring Splint does not afford quantifiable dynamic traction. In summary, it was never designed for emergency use.

In an endeavor to overcome the drawbacks of the Thomas device, particularly for emergency applications, a number of traction splints have been developed, both of the Ring Splint and the Ischial Bar Splint categories.

Among the Ring Splint group is the SAGER ® Emergency Traction Splint, based on U.S. Pat. No. 3,756,227, granted to Joseph A. Sager on Sept. 4, 1973. The SAGER ® Splint is available through Minto Research & Development, Inc. 3676 Charlanne Drive, Redding, Calif. 96002, and affords several of the advantages of the Thomas Full Ring Splint while obviating many of the disadvantages of the Thomas device. It also provides quantifiable dynamic traction.

The padded cushion, or crotch piece, disclosed in the Sager patent, is rectangular in transverse section and is curved in two planes so that the inner surface of curvature in one plane conforms generally to the inside surface of the adjacent thigh while the inner surface of curvature in the other plane curves generally upward to conform to the curvature of the perineum. When applying the splint, the crotch piece is pushed up into the crotch until it fits snugly against the tuberosity of the ischium and the perineum.

Padded cushions, or crotch pieces, are also disclosed in Borschneck Pat. No. 4,350,153, granted Sept. 21, 1982, for Splint For Use With A Human Leg; and Borschneck U.S. Pat. No. 4,608,971, granted Sept. 2, 1986, for Emergency Leg Splint.

Although the padded cushions shown in the above-recited Sager and Borschneck patents have performed in an anatomically and physiologically correct manner, increased patient comfort and favorable response is obtained where the same points of countertraction can be used as in the Thomas Full Ring Splint, namely, the ischial tuberosity, the ischial and pubic ramus and symphysis pubis.

The present splint cushion provides these advantages.

SUMMARY OF THE INVENTION

A preferred embodiment of the present invention comprises an elongated, saddle-shaped cushion capable of being selectively bent laterally into a V-shaped or arcuate configuration similar to the operative portion of the Thomas Full Ring when fully applied to the four countertraction points.

Both thin and obese patients can be accommodated.

The patient's legs need not be lifted; and it is not necessary to thread the patient's leg through a ring as is the case either in applying or removing a splint of the full ring or half ring type.

Traction can be applied in seconds and is never lost because the present perineal cushion forms a secure, well-positioned saddle for the pelvis. The ability to bend and conform the cushion laterally allows the cushion to be fitted to the patient so that countertraction forces are distributed over several regions. Patient comfort as well as security of installation are thereby enhanced.

In order to provide yieldability, an internal elongated core either of bendable material or of hinged plate construction is provided. The core is covered by padding, such as of foamed polyurethane or foam rubber or gel material. The upper and side surfaces of the pad are rounded and are curved to define an elongated saddle with a modified hour glass shape in plan. The pad impinges on, or bears, or presses against, the four regions of the pelvis set forth above in connection with the full ring splint when the cushion is bent laterally as applied.

Projecting from the lower surface of the cushion is an external continuation of the core plate, the extension providing a connector, arranged to fit on the adjacent end portion of the longitudinal tube of the splint.

Also formed in the external continuation of the plate, adjacent the opposite ends thereof, is a pair of parallel elongated slots accommodating the bight portion of a webbing with a buckle, or with a VELCRO ® fastener, enabling the splint to be firmly secured to the upper thigh of the fractured limb.

DESCRIPTION OF THE DRAWING FIGURES

FIG. 2 is a front elevational view, the rear elevation being substantially a mirror image of the figure shown;

FIG. 3 is a top plan view;

FIG. 4 is a bottom plan view;

FIG. 5 is an elevational view of the right-hand end in FIG. 2;

Figure 1:
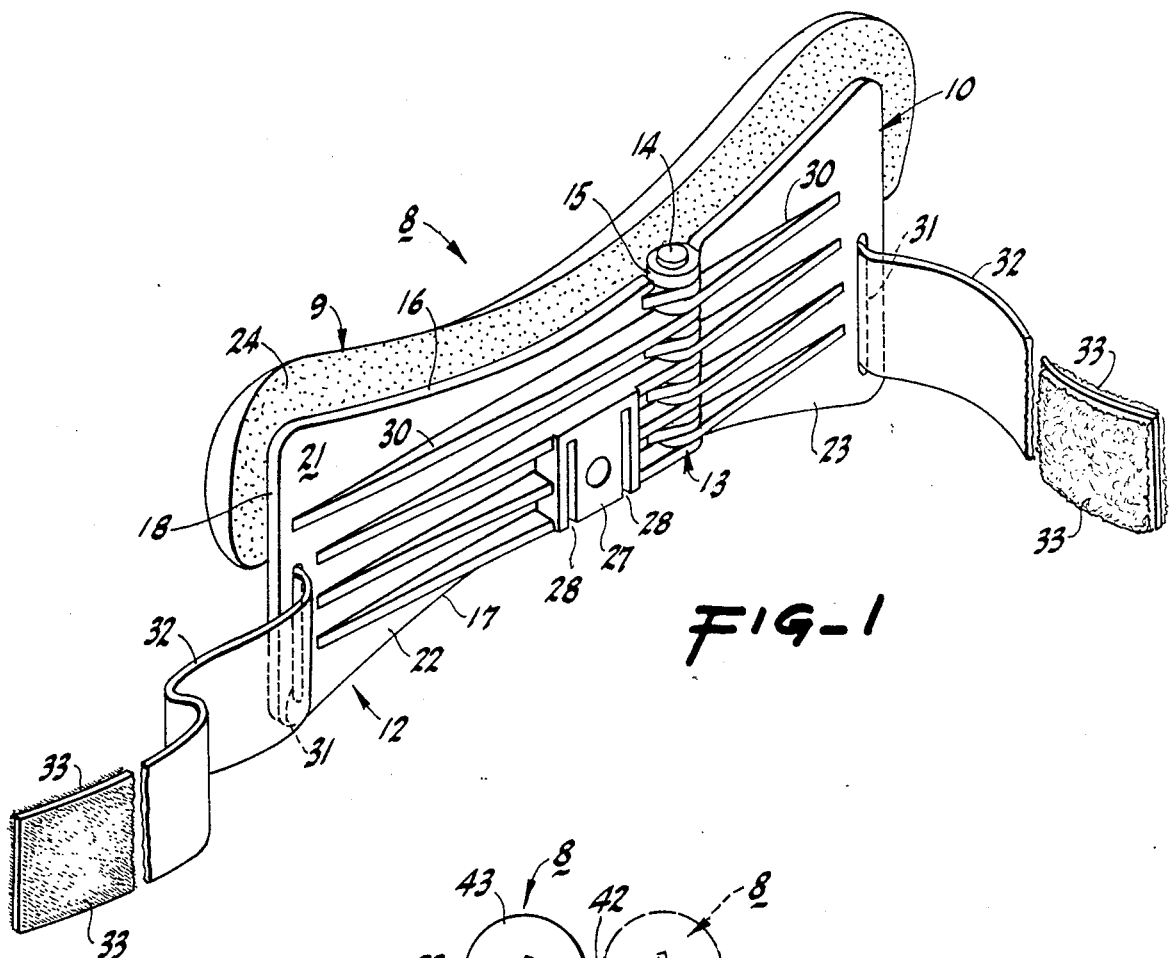
FIG. 1 is a perspective view to a cushion embodying the various features of the present invention, the cushion being shown in linear configuration preparatory to being bent to non-linear configuration when the splint is being fitted to a patient, and with portions broken away to reveal interior details.
Figure 7:
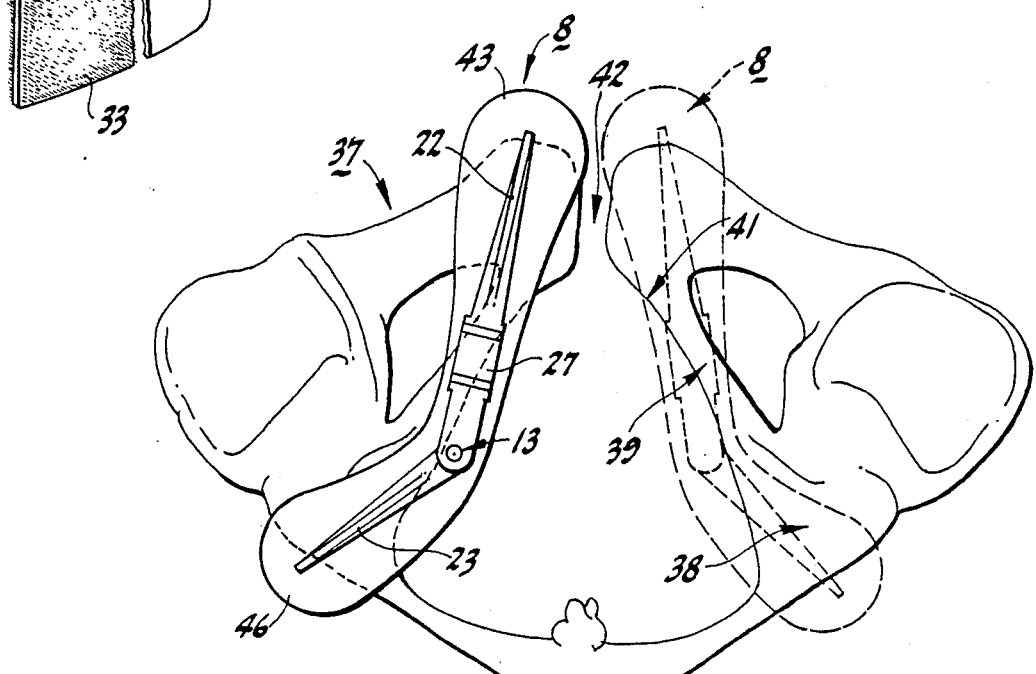

FIG. 6 is a transverse section of the pad only, taken on the line 6—6 in FIG. 3; and, FIG. 7 is a bottom plan view of a human pelvis, to a reduced scale, illustrating the location of the four pelvic regions of countertraction when traction is applied to the emergency splint on which the present cushion is mounted, and showing in full line the cushion bent to one side and, in broken line, the cushion bent to the other side.

DETAILED DESCRIPTION

While the perineal cushion of the invention is susceptible of several different variations, depending upon the environment and requirements to use, it has been successfully embodied in the form disclosed in the following description and accompanying views of the drawing.

The cushion of the invention, generally designated by the reference numeral 8, has been developed as an improvement over the substantially linear countertraction cushions heretofore used on emergency fraction splints of the general kind disclosed, for example, in Joseph A. Sager U.S. Pat. No. 3,756,227, issued Sept. 4, 1973.

The present cushion is characterized by its compliance to being selectively bent to assume a desired one of a variety of shapes in order to distribute, in optimum fashion, the countertraction force exerted by the splint as traction is applied in order to maintain alignment of a fractured leg bone.

In overall aspect, the cushion 8 includes an elongated, end-lobed body 9 having an internal core portion 10 covered with padding and an unpadded projecting core portion 11 serving to connect the cushion to the splint and to hold a thigh strap. The internal portion 10 and the external portion 11 are together, termed a core 12, or plate, or base, and is constructed of a plastic material, such as polyethylene or of metal.

In the form of device illustrated in the Figures, compliance, or bendability, of the cushion 8 is attained by hinging together two sections of the core 12. Hinging is afforded by a hinge 13 including a hinge pin 14 fitting very tightly in the circumscribing walls of the hinge sockets 15 formed on the respective sections.

In side profile, as appears most clearly in FIG. 2, the core 12 includes a concave upper edge 16 and a concave lower edge 17. The core 12 extends between opposite ends 18 and 19 and includes opposite side faces 21. The core 12 comprises a long section 22 and short section 23, the abutting portions of the sections 22 and 23 being joined along the hinge 13.

The upper or interior portion of the core 12 is covered by a pad 24 of protective, resilient, padding material for greater comfort where the cushion exerts countertraction force against the patient's perineum.

The padding 24 can be of any suitable resilient material, such as foamed polyurethane or foam rubber or a hydrostatic action gel of the kind used, for example, in many bicycle seats. The interior of the pad 24, as can be seen most clearly in FIG. 6, is formed to accommodate the internal portions of the core and includes a cruciform slot 25 to receive the plate and the laterally projecting stiffening ribs 30 of the hinge structure.

In order to mount the cushion 11 on the proximal end of the hollow, rectangular-in-section splint tube 26, the long portion 22 of the core 12 is shaped to provide a central, rectangular-in-section boss 27 flanked and defined by a pair of parallel recesses 28. The boss 27 receives the end 26 of the hollow splint tube and the boss and tube end are secured by a fastening, such as a bolt (not shown) passing through an opening 29 in the boss 27 in register with an opening in the tube end 26.

A pair of parallel slots 31 near the ends 18 and 19 of the core 12 receive an adductor bridle 32, or thigh strap, having its bight threaded through the slots 31. The ends of the bridle are provided with a fastener, such as a VELCRO ® fastening 33, or a buckle, enabling the strap 32 to secure the cushion 11 to the patient's upper thigh of the fractured limb after the cushion is fitted in place as illustrated in FIG. 7. The fastening 33 is operable in either direction of the bridle, i.e. either thigh can be secured.

FIG. 7 shows the four countertraction points on the bottom of the pelvis 37, namely, the ischial tuberosity 38, the ischial ramus 39, the pubic ramus 41 and the midline symphysis pubis 42. By distributing the countertraction forces over these four points, or regions, the force impinging on each region is diminished and the patient's discomfort is lessened accordingly.

The cushion 8 can be bent in either direction as can be seen by the full line and the broken line representations in FIG. 7.

As will be noted, the cushion 8 in top plan is of a modified hour glass configuration, with a lobe 43 on one end 44 and a lobe 46 on the other end 47. Intermediate the ends 44 and 47, the cushion narrows to a saddle-shaped isthmus 48. Owing to the fact that the lobe 43 is on the longer section 22 of the core 12 and the lobe 46 is on the shorter section 23 of the core 12, the lobe 43 is longer than the lobe 46 when the two lobes 43 and 46 are angled relative to each other, as shown in FIG. 7.

The hinge 13 enables the longer lobe 43 to be set at an angle relative to the shorter lobe 46 when the splint is applied, the hinge 13 being located approximately one-third of the distance from the end 47 to the end 44.

The hinge pin 14 is dimensioned so as to form an interference fit with the circumscribing walls of the hinge sockets 15, thereby frictionally causing the long section 22 of the core to remain at the angle to which it was rotated relative to the short section 23 of the core 12.

It is to be noted at this juncture, that while the rigid plate 12 and hinge 13 combination described above affords a reliable means for bending, or deflecting, the long lobe 43 relative to the short lobe 46 it would also be feasible to make the core of a bendable material, such as annealed lead or other malleable metal which retains the shape into which it is bent.

To assemble the core 12 to the pad 24 and thereby form the cushion body 9 the bottom of the pad 24 is spread apart, enlarging the cruciform slots 25 so as to receive the conjugate internal portion 10 of the core, then releasing the pad and allowing the pad 24 to return into snug relation with the internal portion of the core 12. The use of an adhesive to seal the pad to the core is not ordinarily required, depending upon the resilience of the pad. Once the pad closes, the head of the hinge pin 14 is captured.

The thigh strap 32 is threaded through the slots 31 and the cushion is mounted on the end 26 of the splint.

In positioning the splint and attached cushion to a patient in supine attitude, the splint is placed between the patient's legs in the perineal region with the short lobe 46 downward and bent toward the side which carries the fractured leg. As shown in FIG. 7, the cushion can be bent in either direction.

The cushion is located against the perineum with the deflected short lobe 46 resting against the ischial tuberosity 38 and the long lobe 43 above or against the midline symphysis pubis 42. The intermediate portions of the cushion will then be properly located in the vicinity of the ischial ramus 39 and the pubic ramus 41, and possibly as high as the symphysis pubis 42.

The adductor bridle 32, is thereupon applied around the upper thigh of the adjacent fractured limb and secured by the fastening 33. After traction is administered, it is advisable to tighten the bridle, or thigh strap, 32 on the upper thigh before applying any additional binding in order to make the patient ready for transport.

The cushion body 10 retains its approximately arcuate, or V-shaped configuration against the four critical countertraction points, not only as a result of the tight hinge pin construction but also as a result of the secure anchoring afforded by the tightened adductor bridle or thigh strap 32.

It can therefore be seen that the advantages of the well-known SAGER ® Splint have been extended to afford even greater splint security and comfort to the patient by enlarging the number of countertraction regions engaged by the perineal cushion.

What is claimed is:

1. Ischial perineal cushion for emergency traction splint used to maintain alignment of fractured leg bone comprising:
   a. an elongated body extending longitudinally between opposite ends and transversely between opposite sides and between an upper surface and a lower surface, said body being compliant and being laterally bendable to a permanent predetermined non-linear configuration in which said upper surface bears only against the pelvis in countertractive position, said body being a modified hour glass shape in plan with two enlarged end lobe portions and an intermediate constricted portion, and in which said upper surface of said body is saddle-shaped in side elevation;
   b. means for connecting said body to the emergency traction splint; and,
   c. a bridle closable at opposite ends by an adjustable fastener, said bridle being dimensioned to secure said cushion in fitted position with said cushion in countractive position only against the pelvis.

2. A cushion as in claim 1 in which one lobe portion is longer than the other lobe portion.

3. A cushion as in claim 1 in which said body includes an elongated core of compliant material bendable to a non-linear shape; and a pad covering at least said upper surface of said body.

4. A cushion as in claim 1 in which said body includes an internal elongated plate articulated by a hinge located intermediate the ends of said plate; and an external pad constructed of resilient padding material.

5. A cushion as in claim 4 including means for maintaining the non-linear configuration of said body at a predetermined angular displacement.

6. A cushion as in claim 5 in which said maintaining means includes a hinge having a plurality of hinge pin sockets and a hinge pin in interfering relation with the circumscribing walls of said hinge pin sockets.

7. A cushion as in claim 4 in which said hinge is located approximately one third of the distance between said ends of said plate and said plate is longitudinally centered in said pad so that when said body is bent to non-linear configuration said cushion comprises a first and second lobe with said first lobe approximately twice the length of said second lobe.

8. A cushion as in claim 7 in which the non-linear configuration of the bent body is substantially V-shaped.

* * * * *